(12) United States Patent
Sluss et al.

(10) Patent No.: US 8,512,411 B2
(45) Date of Patent: Aug. 20, 2013

(54) TRAPEZOIDAL BONE PLUGS AND METHOD OF BONE-TENDON-BONE ACL RECONSTRUCTION

(75) Inventors: Robert K. Sluss, Naples, FL (US); James P. Bradley, Pittsburgh, PA (US)

(73) Assignee: Arthrex, Inc., Naples, FL (US)

( * ) Notice: Subject to any disclaimer, the term of this patent is extended or adjusted under 35 U.S.C. 154(b) by 334 days.

(21) Appl. No.: 12/748,100

(22) Filed: Mar. 26, 2010

(65) Prior Publication Data
US 2010/0249939 A1 Sep. 30, 2010

Related U.S. Application Data

(60) Provisional application No. 61/165,351, filed on Mar. 31, 2009.

(51) Int. Cl.
*A61F 2/38* (2006.01)
*A61F 2/28* (2006.01)

(52) U.S. Cl.
USPC .......... 623/20.18; 623/20.14; 623/20.21; 623/23.61

(58) Field of Classification Search
USPC .......... 623/13.11, 13.12, 13.14, 13.17, 13.18, 623/16.11, 20.14, 20.18–20.2; 606/186, 606/232, 281, 286; 604/399; 424/426; 29/428
See application file for complete search history.

(56) References Cited

U.S. PATENT DOCUMENTS

| 7,427,293 | B2 * | 9/2008 | Nycz et al. | 623/14.12 |
| 2001/0056302 | A1 * | 12/2001 | Boyer et al. | 623/17.15 |
| 2004/0039447 | A1 * | 2/2004 | Simon et al. | 623/13.11 |
| 2004/0193217 | A1 * | 9/2004 | Lubbers et al. | 606/232 |
| 2006/0067971 | A1 * | 3/2006 | Story et al. | 424/426 |
| 2007/0055095 | A1 * | 3/2007 | Chu et al. | 600/37 |

FOREIGN PATENT DOCUMENTS
EP 1 642 602 A2 4/2006

OTHER PUBLICATIONS

510(k) Summary—OSferion, Jan. 25, 2007, (6 pages).

* cited by examiner

*Primary Examiner* — David Isabella
*Assistant Examiner* — Yashita Sharma
(74) *Attorney, Agent, or Firm* — Dickstein Shapiro LLP

(57) ABSTRACT

A method of synthetic grafting of bone-tendon-bone autograft harvest sites using preformed synthetic trapezoidal implants. The implants are formed of tricalcium phosphate, an osteoconductive bone graft substitute and filler, which allows for simultaneous controlled absorption and promotion of osteogenesis. The implants are preferably pretreated or presoaked intraoperatively in autologous blood, or autologous conditioned plasma, or bone marrow aspirate products to enhance healing ability. The implants are trimmed to match the patellar pole shape, pressed into place in the bone voids, and oversewn to complete the procedure.

6 Claims, 4 Drawing Sheets

TRAPEZOIDAL BONE PLUGS AND METHOD OF BONE-TENDON-BONE ACL RECONSTRUCTION

CROSS-REFERENCE TO RELATED APPLICATIONS

This application claims the benefit of U.S. Provisional Application No. 61/165,351 filed on Mar. 31, 2009, the entire disclosure of which is incorporated by reference herein.

FIELD OF THE INVENTION

The present invention relates to the field of surgery reconstruction, particularly, to a method and system of implants for filling bone voids during arthroscopic surgery.

BACKGROUND OF THE INVENTION

Anterior cruciate ligament (ACL) reconstruction surgeries are well-known in the art. In general, the ACL reconstruction involves drilling a tunnel through the tibia, drilling a closed tunnel (socket) into the femur, inserting a substitute ACL graft (for example, a bone-tendon-bone (BTB) graft) into the tunnels, and securing the graft to the walls of the tibial and femoral tunnels using interference screws or the like.

In patients who undergo BTB ACL reconstruction, the BTB graft may be harvested directly from the patient (autograft). These patients typically experience some level of post-operative anterior knee pain in the region of the harvest sites (i.e., patella and the tibial tuberosity), as well as some level of pain while kneeling.

An implant system comprising two implants (one for the patella and one for the tibia) that includes bone void filler material that is preformed into the typical shape of the two bone voids to be filled (harvest sites) is needed. Also needed is a kit with bone void filler materials preformed into the typical shape of the two bone voids (patella void and tibial tuberosity void), the preformed materials being prepackaged into a single package or kit.

SUMMARY OF THE INVENTION

The present invention provides methods, systems and instruments for forming prepackaged, off-the-shelf osteoconductive or osteoinductive synthetic grafts for autograft BTB harvest sites. Preferably, the prepackaged, off-the-shelf synthetic osteoconductive or osteoinductive grafts have a trapezoidal shape that conveniently matches each of the bone block harvest sites (voids). The grafts may be trimmed to fit the voids. The grafts promote bone ingrowth as the bone is fully replaced. The grafts may be pretreated with autologous blood, autologous conditioned plasma and/or bone marrow products.

The system of the present invention includes two trapezoidal-shaped bone void filler synthetic implants with specified dimensions (i.e., cut to appropriate sizes and lengths) that are manufactured out of an osteoconductive or osteoinductive material that promotes new bone growth and replacement of the implants. The bone void fillers of the present invention may be designed with a predetermined density and porosity, to balance strength and solubility. The two trapezoidal-shaped bone void filler synthetic implants are packaged as a single, prepackaged system or kit. The implants may be provided with ribs and/or protuberances on the sides of the implants, to create some interference fit when inserted (pressed) into place.

The prepackaged trapezoidal-shaped bone void filler synthetic implants are prepared and inserted into the respective bone voids in the patella and tibia by a specific method. The preparation and insertion method is critical to preserve normal anatomy and prevent implant shifting and dislodging.

These and other features and advantages of the invention will be more apparent from the following detailed description that is provided in connection with the accompanying drawing and illustrated exemplary embodiments of the invention.

DETAILED DESCRIPTION OF THE PREFERRED EMBODIMENTS

The present invention provides methods, systems and instruments for forming prepackaged, off-the-shelf synthetic osteoconductive or osteoinductive grafts for autograft BTB harvest sites. Preferably, the prepackaged, off-the-shelf osteoconductive or osteoinductive grafts have a trapezoidal shape that conveniently matches each of the bone block harvest sites (voids). The grafts may be trimmed to fit the voids. The grafts promote bone ingrowth as the bone is fully replaced. The grafts may be pretreated with autologous blood, or autologous conditioned plasma and/or bone marrow products.

In an exemplary embodiment, the system of the present invention includes two trapezoidal-shaped bone void filler synthetic implants with specified dimensions (i.e., appropriate sizes and lengths) that are manufactured out of an osteoconductive or osteoinductive material that promotes new bone growth and replacement of the implants. These bone void fillers have a predetermined density and porosity, to balance strength and solubility. The two trapezoidal-shaped bone void filler implants are packaged as a single system. The implants may be provided with ribs and/or protuberances on the sides of the implants, to create an interference fit when inserted (pressed) into place.

The synthetic implants of the present invention are preferably formed of OSferion, which is an osteoconductive bone graft substitute and bone void filler consisting of 100% high purity Beta-tricalcium phophate (β-TCP), sold by Olympus Biomaterial Corporation, 34-3 Hirai, Hinode-machi, Nishitama-gu, Tokyo 190-0182, Japan. OSferion allows for simultaneous controlled absorption and promotion of osteogenesis. OSferion has a micro and macro porous structure that allows for excellent cell communication to promote vascularization, an optimum pore diameter to facilitate cell infiltration, and a compressive force of 15-20 MPs (2900 pounds/inch$^2$).

The single system, prepackaged two trapezoidal-shaped bone void filler synthetic implants are prepared and inserted into the respective bone voids in the patella and tibia by a specific method. The preparation and insertion method is critical to preserve normal anatomy and prevent implant shifting and dislodging.

Figure 1:
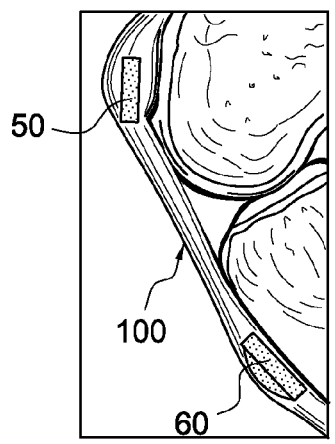
FIGS. 1-3 illustrate various views (including post-operative radiographs) of the bone void filler implant system of the present invention, used for BTB ACL reconstruction.
Figure 2:
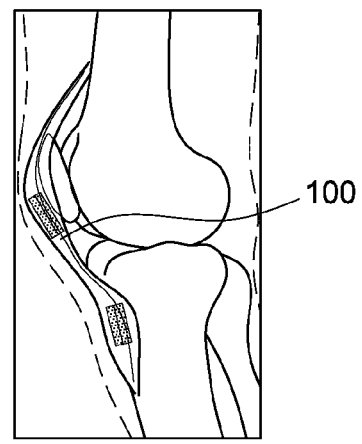
Figure 3:
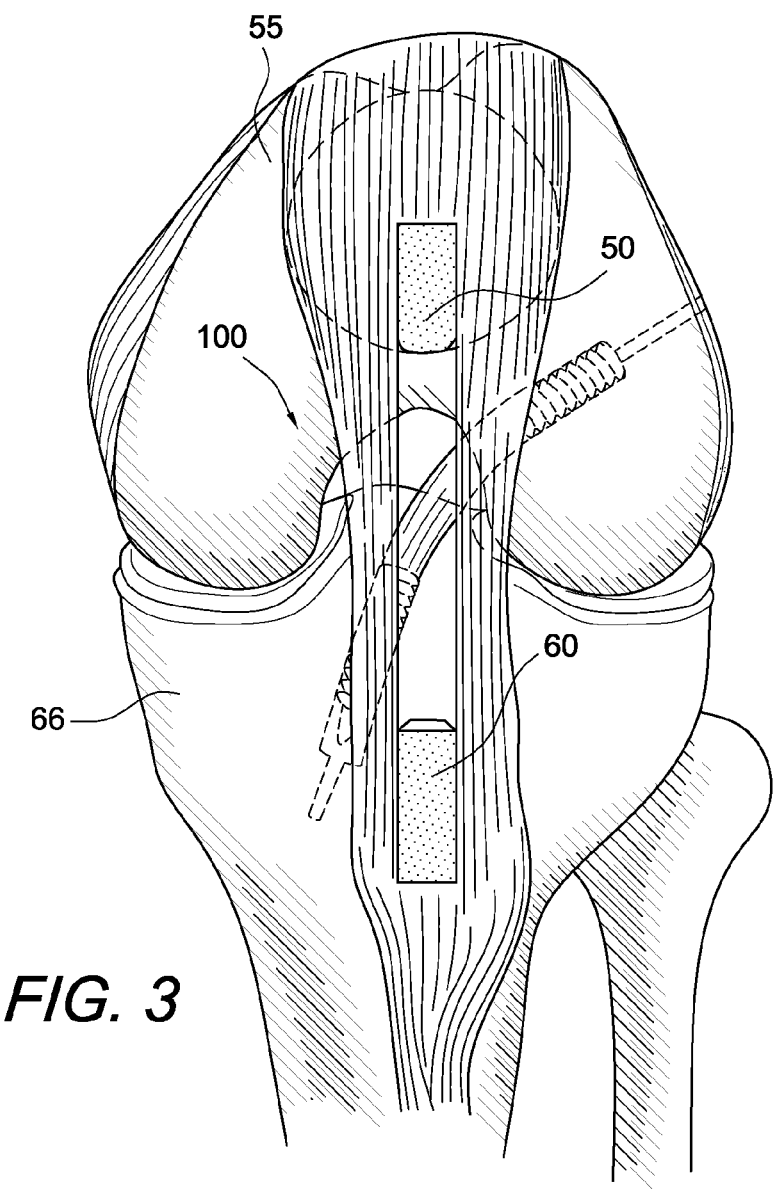

Referring now to the drawings, where like elements are designated by like reference numerals, FIGS. 1-3 illustrate system 100 of the present invention including two trapezoidal-shaped bone void filler implants 50, 60. The trapezoidal-shaped bone void filler implants 50, 60 are provided as a prepackaged, off-the-shelf system (i.e., as a single package or single kit) with each of the filler implants conveniently matching the shape and configuration of the bone block harvest sites (recipient sites or voids) to fill. In the exemplary embodiment shown in FIGS. 1-3, the trapezoidal-shaped bone void filler implant 50 has the shape and configuration of the patellar void to be filled (in the patella 55) and the trapezoidal-shaped bone void filler implant 60 has the shape and configuration of the tibial void to be filled (in the tibia 66).

The trapezoidal-shaped bone void filler implants 50, 60 are preferably trimmed to fit the recipient sites. One advantage is that the implants 50, 60 promote bone ingrowth as the bone is fully replaced. Preferably, the grafts 50, 60 are pretreated with autologous blood, or autologous conditioned plasma, and/or bone marrow products prior to insertion into the respective sites. Treatment of the implants 50, 60 with autologous blood, or autologous conditioned plasma, and/or bone marrow products is preferably conducted intra-operatively (i.e., subsequent to the removal of the implants from the package and prior to insertion).

Figure 10:
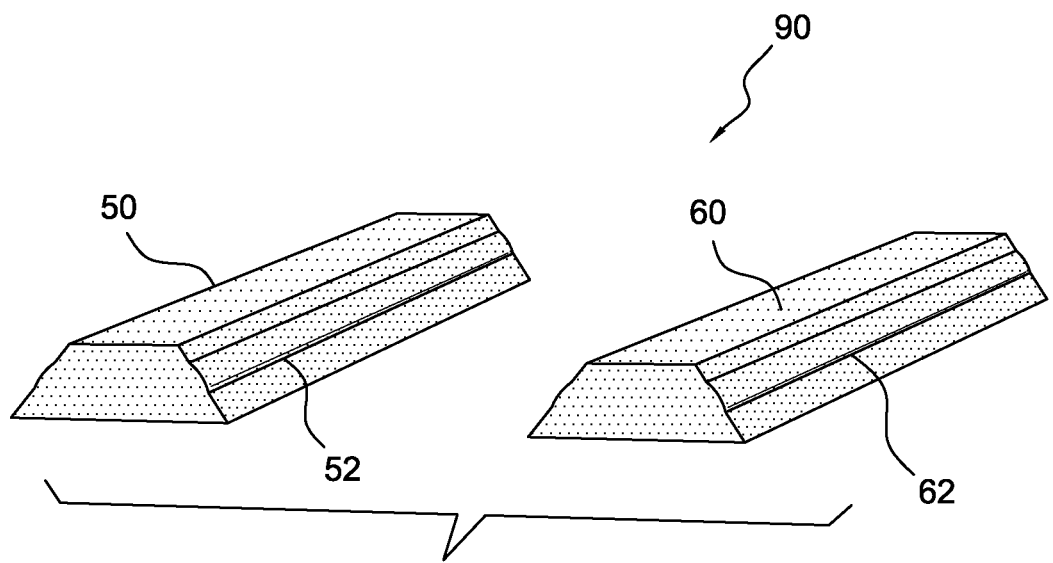
FIG. 10 illustrates a set of implants with ribs.

In FIG. 10, the two trapezoidal-shaped bone void filler implants 50, 60 may be packaged in a single kit 90. The implants 50, 60 may also be provided with ribs and/or protuberances 52, 62 on the sides of the implants, to create some interference fit when inserted (pressed) into place.

An exemplary method of preparation and insertion of the system 100 of the present invention is detailed below with reference to specific steps and shown in FIGS. 4-9:

After the BTB autograft has been harvested from the patient, the base of each void in the patella and tibia are leveled off using morselized or slivered bone remnants from preparing the BTB graft or similar bone void filler.

Next, the appropriate sized trapezoidal shaped bone void filler 50, 60 is chosen to fill each bone void.

Figure 4:
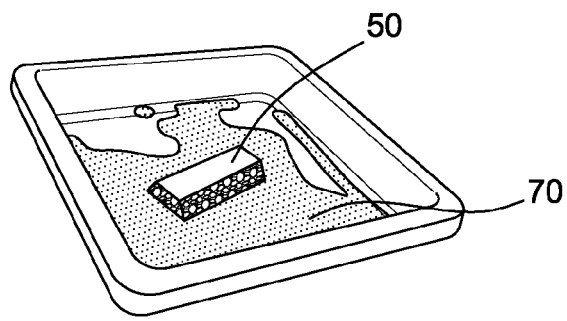
FIG. 4 illustrates an implant pretreated or presoaked in autologous blood.

The implants 50, 60 are then pretreated or presoaked in autologous blood, or autologous conditioned plasma, or bone marrow aspirate products to enhance healing ability. FIG. 4 shows patellar implant 50 being presoaked in autologous blood 70.

Figure 5:
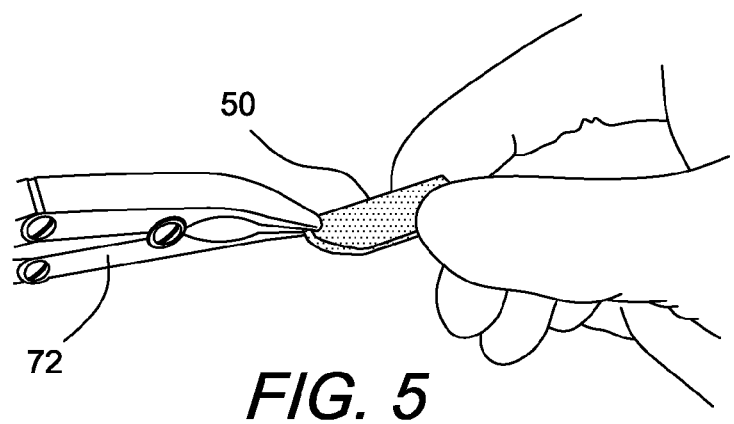
FIG. 5 illustrates an implant being trimmed.
Figure 6:
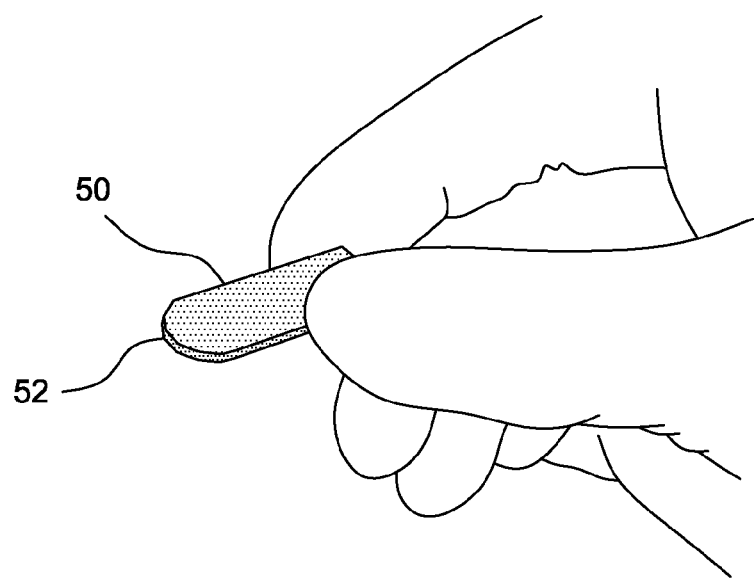
FIG. 6 illustrates a curved trimmed side of an implant.

Next, each trapezoidal shaped bone void filler is trimmed to match the surrounding bony anatomy. FIG. 5 shows patellar implant 50 being trimmed by trimmers 72. The distal portion of the patellar implant 50 is rounded to match the rounded geometry of the distal pole of the patella. This rounding is crucial in maintaining normal anatomy. FIG. 6 shows the rounded portion 52 of the patellar implant 50. In another embodiment the implants are pretreated or presoak after they are trimmed.

Figure 7:
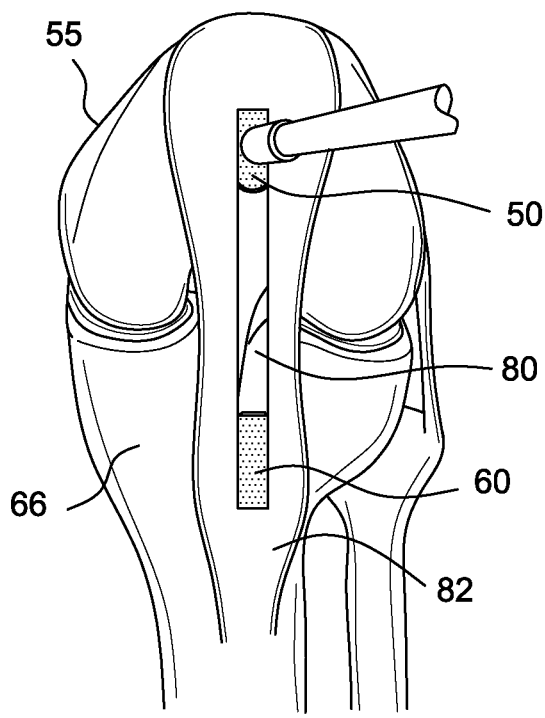
FIG. 7 illustrates implants set in the patellar and tibia bones.

After being trimmed, the patellar implant 50 is inserted into the void in the patellar bone by hand until seated. In another embodiment, the patellar implant 50 is inserted into the void of the patellar bone 55 by an instrument as shown in FIG. 7. The patellar implant 50 is inserted into the patellar bone 55 by passing through opening/defect 80 in patellar tendon 82.

The tibial implant 60 is also inserted by hand until fully seated in a void in the tibial bone 66. In another embodiment, the tibial implant 60 is inserted into the void of the tibial bone 66 by an instrument. A fully seated tibial implant 60 is shown in FIG. 7. The tibial implant 60 is also inserted by passing through defect 80 in the patellar tendon 82.

Figure 8:
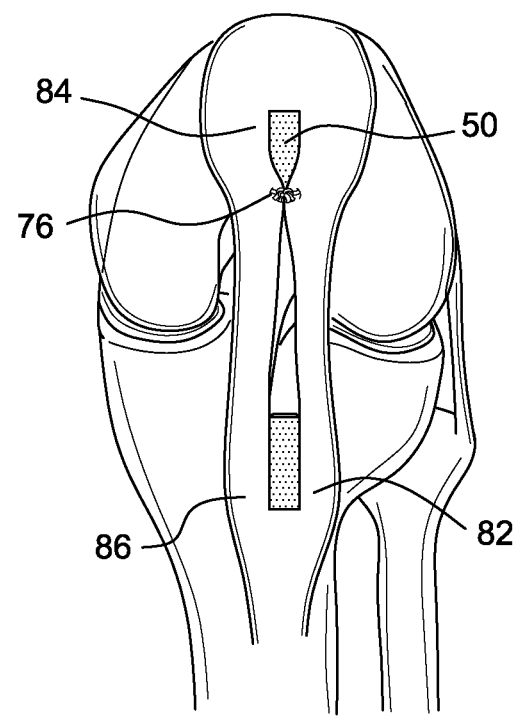
FIG. 8 illustrates a single suture being used to close a patellar tendon defect.

After the implant 50 has been seated an absorbable or nonabsorbable suture 76 is used to close the defect on the proximal side 84 of the patellar tendon 82 at the distal portion of the patellar implant 50 to increase stability of the implant 50 as shown in FIG. 8.

Figure 9:
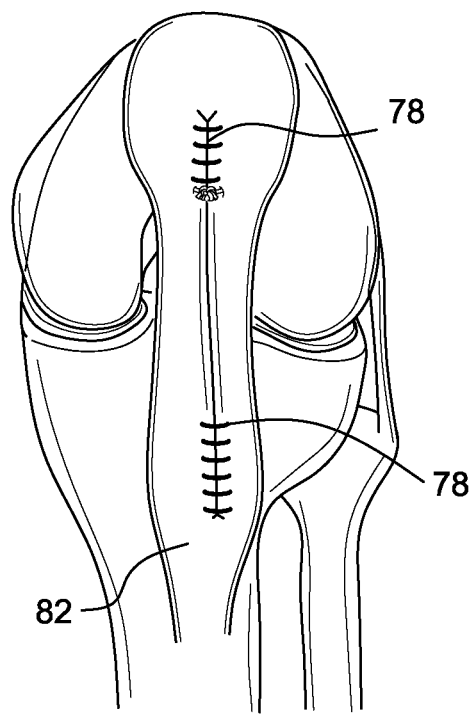
FIG. 9 illustrates implants that have been completely oversewn.

Next the periosteum and soft tissue are oversewn over the remainder of the visible patellar implant 50 for increased stability as shown in FIG. 9.

Subsequently, distal portion 86 of the defect 80 of the patella tendon 82 at the proximal end of the tibial implant 60 is closed using an absorbable or nonabsorbable suture 78 to provide stability to the tibial implant 60 as shown in FIG. 9.

The periosteum and soft tissue are oversewn over the remainder of the visible tibial implant 60 for increased stability as shown in FIG. 9.

In another embodiment, the patellar implant 50 is set and oversewn before the insertion of the tibial implant 60. In another embodiment, the tibial implant 60 is set and oversewn before the insertion of the patellar implant 50. In another embodiment, both the patellar implant 50 and the tibial implant 60 are set and a single suture is sewn over both the patellar implant 50 and the tibial implant 60 before either the pateller implant 50 or tibial implant 60 is completely oversewn.

Although the system, kit and method of the present invention have been described above with reference to a specific ACL reconstruction, the system, kit and method of the present invention may also be employed for additional reconstructive procedures, such as tibial plateau fractures and calcaneous fractures, among others.

Although the present invention has been described in relation to particular embodiments thereof, many other variations and modifications and other uses will become apparent to those skilled in the art.

What is claimed as new and desired to be protected by Letters Patent of the United States is:

1. A method of surgery comprising:
   providing first and second solid trapezoidal-shaped implants consisting of tri-calcium phosphate, the implants each having a proximal end and a distal end, wherein the first solid implant is preformed into the typical shape of a bone void in the patella, and wherein the second solid implant is preformed into the typical shape of a bone void in the tibia;
   trimming the distal end of the first solid implant to be rounded to match a rounded geometry of a distal pole of a patella;
   after trimming, inserting the first solid implant into the bone void in the patella that is beneath an opening in a tendon, the opening having first and second sides;
   inserting the second solid implant into the bone void in the tibia that is beneath the opening in the tendon; and
   joining the first and second sides of the opening in the tendon that are near the distal end of the first implant.

2. The method of claim 1, further comprising joining the first and second sides of the opening in the tendon that are between the proximal and distal ends of the implant.

3. The method of claim 1, wherein the first and second implants have ribs.

4. The method of claim 1, wherein the opening in the tendon is joined by a suture.

5. The method of claim 1, wherein the opening in the tendon is formed as a result of a graft being taken from the tendon.

6. The method of claim 5, wherein the bone voids in the patella and tibia are formed as a result of a graft being taken from the tendon with attached bone pieces.

* * * * *